United States Patent [19]

Donaldson et al.

[11] Patent Number: 4,552,559
[45] Date of Patent: Nov. 12, 1985

[54] APPLICATORS

[75] Inventors: John H. Donaldson; Robert Brunswick; Andrew J. Foulkes, all of Melbourne, Australia

[73] Assignee: Wellcome New Zealand Limited, Auckland, New Zealand

[21] Appl. No.: 669,731

[22] Filed: Nov. 8, 1984

Related U.S. Application Data

[63] Continuation of Ser. No. 441,430, Nov. 15, 1982, abandoned.

[30] Foreign Application Priority Data

Nov. 24, 1981 [NZ] New Zealand ........................ 199049
Aug. 30, 1982 [NZ] New Zealand ........................ 201756

[51] Int. Cl.⁴ ............................................. A61M 5/00
[52] U.S. Cl. ..................................................... 604/198
[58] Field of Search ................ 604/198, 197, 131–137, 604/46, 47, 185, 186, 273

[56] References Cited

U.S. PATENT DOCUMENTS

| | | | |
|---|---|---|---|
| 2,408,323 | 9/1946 | Lockhart | 604/198 |
| 3,051,173 | 8/1962 | Johnson et al. | 604/156 X |
| 3,055,362 | 9/1962 | Uytenbogaat | 604/197 X |
| 3,353,537 | 11/1967 | Knox et al. | 604/186 |
| 3,943,927 | 3/1976 | Norgren | 604/197 |
| 4,067,334 | 1/1978 | Haller | 604/157 |
| 4,403,989 | 9/1983 | Christensen et al. | 604/137 |

Primary Examiner—John D. Yasko
Attorney, Agent, or Firm—Donald Brown

[57] ABSTRACT

The subject matter relates to an applicator for applying matter to be applied, such as vaccine, to animals. The applicator includes an applicator head which incorporates a chamber and needle. The needle is at least partially surrounded by a generally elongate proboscis or cover which is capable of axial movement over and relative to the needle. A reservoir for matter to be applied or vaccine, is provided and is attached to the applicator head. Valving connects the chamber with the needle and also connects the reservoir with the chamber. Predetermined axial movement of the proboscis or cover relative to the needle opens the valving between the needle and chamber and allows matter within the chamber, such as vaccine, to be passed from the chamber through the needle. The chamber is provided with a movable wall and actuating means connected to a trigger. On the trigger being actuated, the spring biased actuating means causes the movable wall of the chamber to move outwardly thereof, opening valving between the reservoir and chamber and drawing an amount of matter to be applied or vaccine into the chamber. A measure or shot of matter to be applied is then held in the chamber until the valve between the chamber and needle is opened on axial movement of the proboscis relative to the needle.

43 Claims, 4 Drawing Figures

APPLICATORS

This application is a continuation of application Ser. No. 441,430, filed Nov. 15, 1982, abandoned.

BACKGROUND OF THE INVENTION

The present invention relates to an applicator and in particular to an applicator suitable for applying matter such as vaccines which are required to be applied by way of injection.

The present invention has particular application to the application of vaccines to animals such as sheep, cattle, pigs and the like. It should however be appreciated that the invention has equal application to the application or injection of matter such as vaccines to humans.

Reference is made throughout the specification and claims to "matter to be applied" and it should be appreciated that this covers vaccines, liquid foodstuffs and other matter that is required to be applied by way of injection.

Up until this time numerous problsm have been associated with the application of matter by way of injection, and in particular problems have arisen in the area of application to animals such as for example sheep, cattle and pigs.

In arrangements provided up until this time, the needle or means for applying the matter has often been exposed.

This has been dangerous from the point of view of the people using the applicator and also dangerous from the point of view of the person or animal being injected. Due to exposed needles, they have often been broken off before, during or after application. This has therefore caused infection and discomfort, as well as being generally inefficient and in some cases expensive.

It has also been a problem with applicators used up until this time, that it has often been necessary and indeed difficult to hold an animal still while applying vaccine. For example, it has often been necessary to first hold the animal, thereafter positioning a needle in the correct or desired position then entering the needle into the animal and thereafter actuating some appropriate means (such as depressing a plunger) to cause matter to be applied to be injected into the animal through a needle. This has been difficult and time consuming.

SUMMARY OF THE INVENTION

The present invention sets out to provide an applicator which overcomes or at least minimises these problems and which also provides a straight forward and efficient applicator for applying matter such as vaccine.

According to one aspect of this invention there is provided an applicator including an applicator head with a chamber and needle; the needle being at least partially surrounded by a generally elongate proboscis mounted for axial movement over the needle; at least one valve being provided between the chamber and the needle; the proboscis being so mounted relative to the chamber and needle, that on predetermined axial movement of the proboscis over the needle, at least an end of said needle is at least partially exposed and valving means between the chamber and the needle opened and means being provided to cause matter to be applied to pass from the chamber through said needle.

According to a further aspect of this invention there is provided an applicator including a reservoir for matter to be applied an applicator head comprising a chamber and elongate needle; the needle being at least partially surrounded by a generally elongate proboscis mounted for axial movement over the needle; at least one valving means being provided between the chamber and the needle; further valve means being provided between the reservoir and the chamber; triggering means being provided; actuation of said triggering means causing matter to be applied to be passed from the reservoir into the chamber; the proboscis being so mounted relative to the chamber and needle, that on predetermined axial movement of the proboscis over to the needle, at least one end of said needle is at least partially exposed, said valving between the chamber and needle is opened; means being provided to cause matter to be applied to pass from the chamber through the needle.

BRIEF DESCRIPTION OF THE DRAWINGS

The invention will now be described by way of example only and with reference to the accompanying drawings, wherein.

DESCRIPTION OF THE PREFERRED EMBODIMENTS

Figure 1:
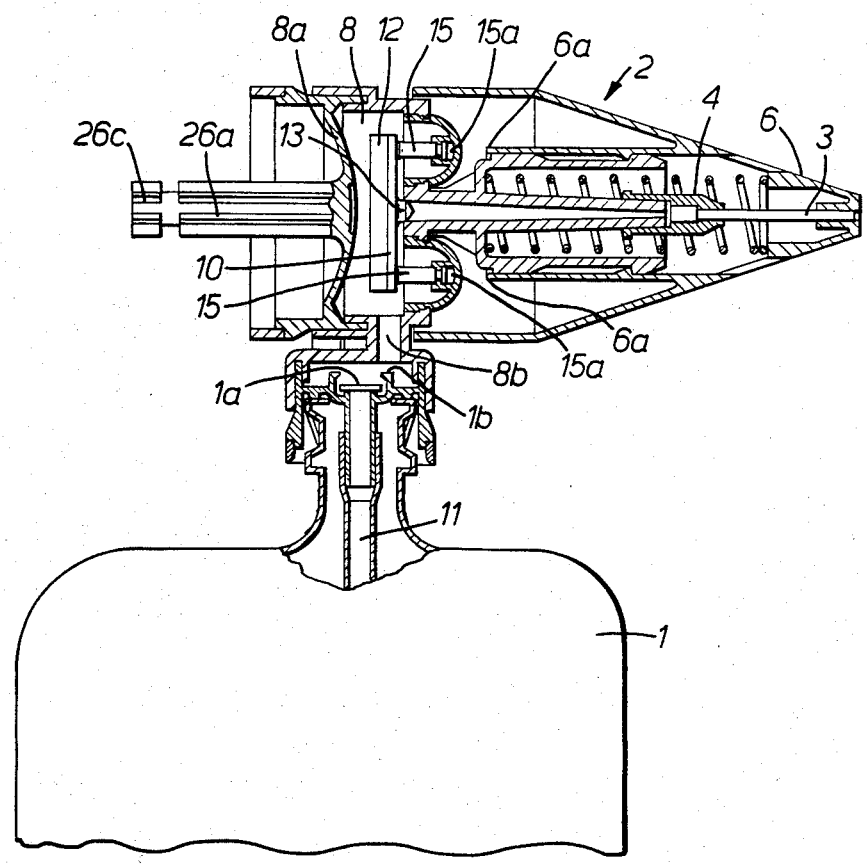
FIG. 1: shows a side exploded view of an applicator head of one form of the invention, connected to an upper portion of a reservoir according to one form of the invention.

Preferably, the present invention provides an applicator for applying matter such as vaccine to animals.

The applicator of the present invention includes a reservoir 1 for vaccine and a head member 2, which are securely attached one to the other in a substantially sealed arrangement. The combined head member 2 and vaccine reservoir 1 are preferably formed of a plastics material and are disposable. It is envisaged that once an amount of vaccine provided in the reservoir 1 has been utilised, the connected or combined head member and reservoir can be disposed of and replaced.

A suitable housing 5 (with reference to FIG. 4 of the accompanying drawings) is provided which locates the head member 2 and reservoir 1 in a substantially releaseable engagement and this will be described hereinafter.

The head member 2 includes a needle or other injection member having a bore therethrough, for the passage of matter to be applied, this hereinafter being referred to as "a needle". An elongate needle 3 is located within suitable guides and mountings 4 and is surrounded by a housing or covering, such as a protective housing, covering or proboscis 6, (hereinafter referred to as a "proboscis"). In the form of the invention shown in the drawings, the proboscis is substantially elongate, conical and tapering in formation, being open at the point end of the needle 3, and located relative to the head member so that it is axially movable relative to the longitudinal axis of the needle 3.

The proboscis 6 substantially covers the length of the needle 3 when not in use.

The head member 2 also provides a vaccine chamber 8, which communicates with the needle 3 by way of valve 10, the valve 10 being located in the head member 2 substantially intermediate the chamber 8 and needle 3.

The valve 10 between the needle 3 and the chamber 8 includes a valve plate 12 and "O" ring 13 adapted to be sealed against a valve seat. Valve actuating means 15 such as arms with buttons 15a on the end thereof, extend outwardly from the valve plate 12, inwardly of the proboscis 6.

The proboscis 6 is formed or provided with an inner skirt portion, which forms a valve actuating portion or means 6a of the proboscis.

When the proboscis 6 is in the position of rest, substantially covering the needle, the valve actuating means 6a of the proboscis and the valve actuating means 15 associated with the valve 10, are spaced apart one from the other.

On movement of the proboscis 6 relative to the needle 3, the valve actuating means 6a of the proboscis is caused to move against the valve actuating means 15 of the valve 10, thus opening the valve 10, between the chamber 8 and the needle 3, and allowing matter to pass from the chamber 8 through needle 3.

The location and spacing of the proboscis relative to the needle and chamber, can be varied, to thus vary the distance required to be travelled by the proboscis before the valving between the chamber and needle is actuated. This then determines the amount of needle to be exposed by actual movement of the proboscis and thus also the depth to which the needle can penetrate through the skin of the animal.

In this way, it will be appreciated that the required depth or amount of penetration of the needle can be varied or determined. Thus, axial movement of the proboscis 6 will not actuate valving between the chamber 8 and needle 3 (to thus deliver a shot or measure of vaccine), until the predetermined amount of needle 3 has been exposed and thus until the needle has penetrated the skin of an animal to the desired depth.

Thus, if for example the needle cannot penetrate to the correct depth, having regard for example to a bone being struck or if the injector or needle is placed against a resisting surface, vaccine delivery is prevented.

The chamber 8 is designed to hold a shot or measure of vaccine for delivery into an animal through the needle 3.

On axial movement of the proboscis 6 relative to the needle 3, the proboscis which is preferably spring biased, moves against the bias of the spring toward the chamber 8, so that the valve actuating means 6a of the proboscis 6 come into contact with the valve actuating means 15 of the valve 12, between the chamber 8 and needle 3. This will then cause the valve 10 and "O" ring 13, to move away from the valve seat to thus communicate the chamber 8 with the needle 3. The measure or shot of vaccine will then be caused to pass from the chamber 8 through the needle 3, to be discharged into an animal.

The reservoir 1 and head member 2 are preferably connected in a permanent or semi-permanent sealed connection, and a passage way 8b is provided to connect the chamber 8 with the reservoir 1.

A feed tube 11 preferably leads up from within the reservoir 1, and is connected to an outlet and a valve 1a and the upper end of the reservoir, which is connected to the chamber 8 by the passageway 8b.

The valve 1a between the reservoir 1 and chamber 8 is preferably a non-return valve.

The chamber 8 is formed with one wall 8a as a movable or flexible wall, which can for example be in the form of a flexible diaphragm, a piston or a ram. These are by way of example only however.

Preferably, the wall 8a is in a form of a flexible diaphragm, preferably constructed of a flexible plastics material, which is sealed to the chamber 8 so as to form a sealed but flexible wall which is capable of movement inwardly and outwardly of the chamber 8.

The movable wall 8a is connected to or formed with spring biased actuating means 26, the actuating means 26 being biased so as to extend the flexible diaphragm 8a into a position in which it extends inwardly into the chamber 8. A first actuating member 26a is connected to the rear side of the diaphragm 8a and is releaseably engageable or locatable with a second actuating member 26b which provides the spring bias referred to hereinbefore, when the first and second actuating members 26a and 26b are interconnected.

The flexible diaphragm 8a is also naturally biased into a position into which it extends inwardly of the chamber 8.

On operation of the actuating means 26, as will be described hereinafter, the flexible diaphragm 8a is pulled outwardly of an chamber 8 against the bias of the actuating spring 27, thus drawing the non-return valve 1a between the reservoir 1 and head member 2 upwardly and open within its guides 1b, FIG. 1, and at the same time sucking or drawing up vaccine from within the reservoir. The outward movement of the diaphragm 8a then sucks or draws a measure or shot of vaccine up into the chamber and when it is in the chamber the pressure of the vaccine forces the non-return valve 1*a* between the reservoir 1 and head member 2 back down into its closed position to thus close and seal a measure or shot of vaccine within the chamber 8.

The measure or shot of vaccine is then held within the chamber 8 under pressure, between the closed valves 1*a* and 10, and under pressure from the flexible diaphragm 8*a* and the spring biased actuating means 26, which urges the diaphragm 8*a* inwardly of the chamber 8.

In use, once a measure or shot of vaccine has been loaded into the chamber 8, (such as in the manner hereinbefore described), the proboscis 6 is placed against an animal in the desired position and a downward pressure applied to the head member 2 by an operator. This will cause the proboscis 6 to move axially relative to the needle 3 and against the bias of the proboscis spring, such as to bring the proboscis valve actuating means 6*a* into contact with the actuating means 15 of the valve 10 between the chamber 8 and needle 3, this pressure causing the valve 10 between the chamber 8 and needle 3 to be opened. The opening of this valve 10 will cause the measure or shot of vaccine within the chamber 8 to exit from the chamber 8 through the needle 3, with some force, assisted by the spring biased flexible diaphragm 8*a* which will urge the shot or measure of vaccine out of the chamber 8.

The present invention provides for the head member 2 and reservoir 1 to be releaseably locatable within a housing 5, the housing 5 providing also triggering means and actuating means for loading a shot or measure of vaccine into the chamber 8. The housing 5 also provides for a handle grip for use by an operator, and a counting mechanism whereby the operator can keep count on the number of shots or measures delivered by the applicator.

Figure 4:
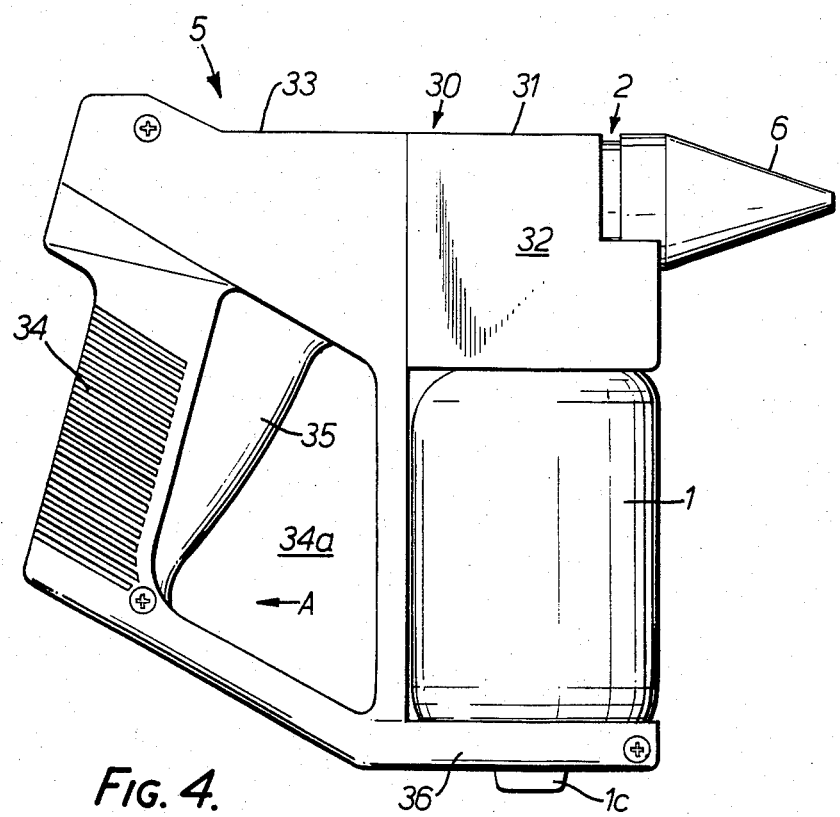
FIG. 4: is a side view of the housing incorporating the head member and reservoir according to one form of the invention.

Referring to FIG. 4 of the accompanying drawings, the housing 5 is shown as incorporating an upper body portion 30, the forward upper body portion 31 being adapted to releaseably locate the head member 2 in appropriate supports and lugs. A front side 32 is hingeably attached to the upper body portion 30 so as to be capable of being opened for location of the head member and closed over and about (and so as to locate) the head member 2 in position. Suitable releaseable locking means such as a locking bolt, clip and the like can be provided, to open and close the front side 32 of the housings. In other forms of the invention, the housing can be provided with a pivotally or hingeably mounted upper wall portion for location and removal of the head member. These are however by way of example only and other variations are envisaged as being possible.

The rear upper body portion 33 locates the actuating means 26 (as hereinbefore referred to) and as will be described further hereinafter.

The rear upper body portion 33 leads into a downwardly extending handle portion 34, which defines a grip opening 34a in which is pivotally located triggering means 35.

The housing further includes a lower body support member which is below, spaced apart from and substantially parallel to the forward upper body portion 31 so as to define a spacing therebetween, in which the reservoir can be located. A suitable slot or recess can be provided in the lower face of the support member 36, in which can be located a tab portion 1c of the reservoir 1.

Figure 2:
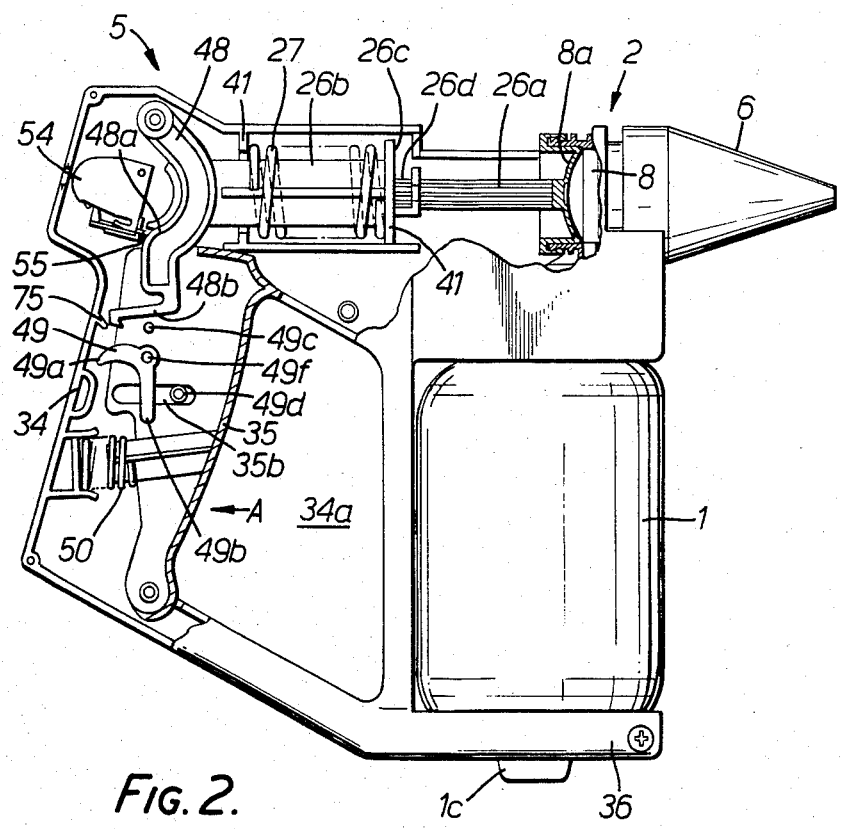
FIG. 2: is a side and partially exposed view of the handle arrangement incorporating the head member and showing the chamber in a substantially loaded condition.
Figure 3:
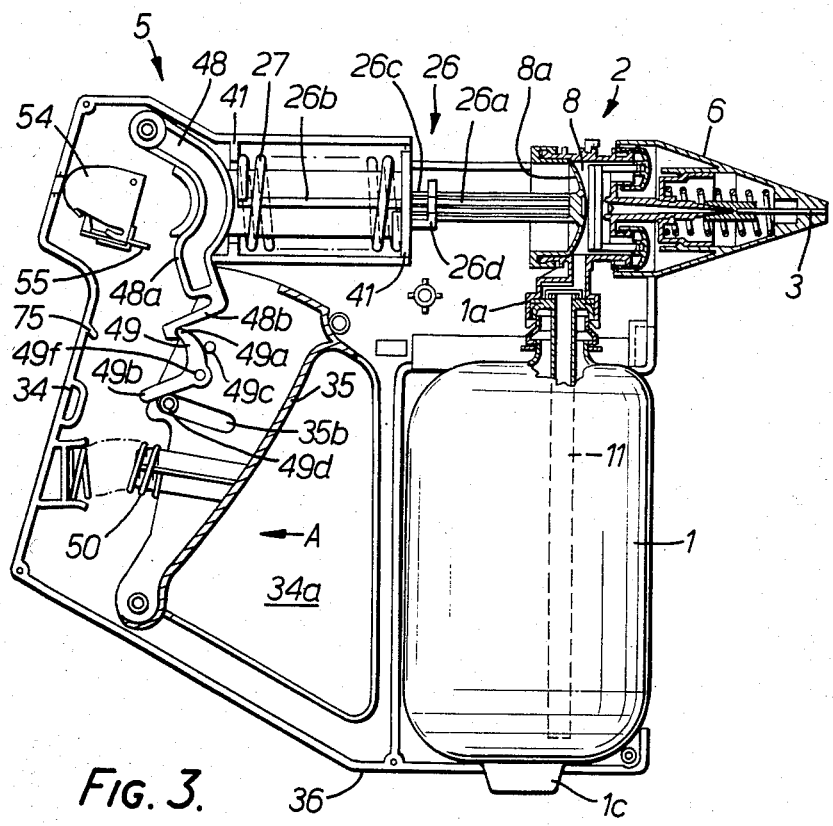
FIG. 3: is a side and partially exploded view of the applicator including the housing and showing the chamber in its released or unloaded position.

Referring further to FIGS. 2 and 3 of the accompanying drawings, these drawings show exploded views of the actuating and triggering mechanism of the applicator as located within the housing 5.

FIG. 2 of the accompanying drawings shows the triggering and actuating mechanisms in position in which the diaphragm 8a of the chamber 8 has been withdrawn and in which a shot or measure of vaccine is within the chamber 8. This is prior to movement of the proboscis 6 relative to the needle 3 and thus the opening of the valve 10 between the chamber 8 and needle 3.

FIG. 3 of the accompanying drawings shows the triggering and actuating mechanisms in position prior to the loading of a measure of shot of vaccine into the chamber 8 and in this position the diaphragm 8a is shown as being in its relaxed position extending inwardly of the chamber 8, in accordance with the urging of the spring bias of the actuating means 26.

The actuating means 26 located within the housing incorporates an actuating member 26b, which is located in the rear portion 33 of the housing 5.

An actuating spring 27 is provided about the actuating member 26b and within spring guides 41 to urge the actuating member outwardly of the housing 5 and towards the chamber 8.

The actuating member 26a is provided with a suitable connection head 26c, to enable it to be releaseably connected to an adjacent slotted end 26d of the actuating member 26b. Thus, on location of the head member 2, and reservoir 1, within the housing 5, the actuating members 26a and 26b are releaseably engaged one with the other.

A trigger 35 is provided and is mounted for pivotal movement, rearwardly, within the grip opening 34a of the handle 34 in accordance with arrow "A" as shown in the accompanying drawings.

The trigger 35 is connected at its upper end, to a pivotally connected crank lever 48 which is connected to a further pivot lever 49 which engages with the lower portion of the crank lever 48 in its position of rest as shown for example in FIG. 3 of the accompanying drawings. A trigger spring 50 connects the trigger 35 and an inner surface of the housing 5, to urge the trigger into its position as shown in FIG. 3 of the accompanying drawings, in which the diaphragm 8a is inwardly of the chamber 8.

A counting mechanism 54 is provided, being provided with an actuating or operating tab or finger 55, the counting mechanism also being provided with a dial or face rearwardly of the housing, which is covered by suitable glass or perspex so that it can be viewed exterior of the housing. A dial capable of showing the number of measures or shots delivered by the applicator is provided and is capable of being seen through the aforementioned glass or perspex. The counting mechanism 54 operates such that on movement or actuation of the finger 55, the counter will be caused to move on one digit, thus keeping a clear indication as to the number of shots or measures.

Referring now to FIG. 3 of the accompanying drawings, the trigger 35 is shown as being in a position of rest and on depression of the trigger, the trigger and the pivotally connected crank lever 48 are caused to move rearwardly. The crank lever 48 is connected to the butt end of the actuating member 26b and thus the movement or depressing of the trigger 35 and movement of the crank lever 48, draws the actuating means 26 away from the chamber and against the bias of the spring 27 passing about the actuating member 26b, this causing the diaphragm 8a to be moved or drawn outwardly of the chamber 8. As described hereinbefore, this opens the valving 1a between the reservoir 1 and chamber 8, sucking or drawing a shot or measure of vaccine into the chamber 8 for delivery. On full depression of the trigger, the crank lever 48 and additional lever member 49 are disconnected such as shown in FIG. 2 of the drawings in which the trigger is disengaged from operation with the actuating means 26.

Referring to FIGS. 2 and 3 of the drawings, the crank arm 48 is formed at its lower end with a substantially flexible hook member or portion 48b.

The trigger 35 pivotally mounts the pivot lever 49, which has two interconnected arms 49a and 49b. The pivot lever 49 is pivotally mounted substantially about its mid point 49f, and is of a substantially bifurcated, splayed or "V" formation.

Free movement or rotation of the pivot lever 49 is prevented by pivot control stops or pins 49c and 49d which allow for pivotal movement of the pivot pin 49 but which restrict movement to prevent free rotation.

The pivot lever 49 is spring biased into a position in which it is biased towards the lower control pin 49d.

An elongate slot 35b is provided in the handle 35 and the control pin 49d extends through the slot. The slot 35b therefore allows for movement of the trigger relative to control pin 49d.

The upper control pin 49c is mounted to and integral with the trigger.

Referring now to FIG. 2 of the accompanying drawings. On the trigger 35 being depressed rearwardly in the direction of arrow "A" in FIG. 2 of the drawings, the engaged arm 49a and hook 48b of the crank arm, are moved rearwardly until the hook 48a of the crank arm 48 comes into contact with the rear wall of the housing, and in particular an abutment 75 on the rear wall of the housing. This then causes the crank arm 48 and pivot lever 49 to disengage one from the other. The depressing of the trigger 35 will cause the pivot lever 49 and connected crank arm 48 to draw the actuating member 26 rearwardly against the bias of the spring 27, and to thus move the movable wall or diaphragm 8a of the chamber 8 rearwardly, this drawing a shot or measure of matter to be applied into the chamber 8.

On the pivot lever 49 and crank arm 48 being disengaged one from the other, the actuating means 26 is able to be free for uninhibited discharge, thus allowing free and uninhibited movement of the actuating means 26, in order to deliver the shot or measure of matter to be applied, irrespective of the trigger position.

On disengagement of the pivot lever 49 and the crank arm 48, the trigger is still able to be depressed such as would be the case when the applicator would be gripped by an operator, who following the applicator being loaded with a measure of charge of vaccine, wishes to grip the applicator firmly, (involving the depressing of the trigger) as he applies the matter to the animal.

On the applicator being applied to an animal such as to deliver a shot in the manner hereinbefore described, and on the valve 10 between the chamber 8 and needle 3 being opened, the urging of the spring biased actuating means 26 against the diaphragm 8a will assist in forcing a measure or shot out of the chamber 8 as soon as the valve 10 opens, this effectively delivering a shot or measure of vaccine through the needle.

Following discharge of the matter from within the chamber, the actuating means 26 and crank arm 48 will return to the position shown in FIG. 3 of the drawings, but the trigger will still be free of engagement with the crank arm 48, and still capable of being depressed.

On the trigger being released, such as being released by an operator, it will be returned such as by trigger spring 50 to the position substantially shown in FIG. 3 of the accompanying drawings, the substantially flexible hook member 48b of the crank arm 48, flexing and riding over the end of the arm 49a of the pivot lever 49, so that the pivot arm 49 and crank lever 48 are interengaged so that a further loading of the applicator can take place.

On the trigger 35 being depressed and on the crank lever 48 being pivoted to move the actuating means 26 rearwardly, an operating or cam face 48a of the crank lever 48 is caused to move against the operating finger 55 of the counting mechanism 54 to thus actuate the counting mechanism to indicate that a shot or measure has been loaded and will be delivered.

It is preferred in this invention that the head member 2 and reservoir 1 are constructed of a plastics material so as to be readily disposable when desired. The housing is preferably, although not essentially, formed or moulded from an appropriate plastics material, so as to be light and straight forward to use and handle. This is however by way of example only.

In one form of the invention, the chamber 8 can be provided with a relief or bleeder valve or opening. Preferably, this is provided in an upper or top side of the chamber 8. The bleeder valve can be in the form of a hole or recess being provided with a suitable closure or cap. In preferred forms of the invention the suitable closure or cap is connected by means of an integral strap, to an adjacent portion of the head member. It has been found in use, that on applying pressure to the reservoir, such as in the form of a "squeeze" matter to be applied will be forced up through the chamber 8 and out of the bleeder valve.

The particular advantage with this is that when an applicator is being used, there may be some air in the reservoir prior to, or during, use. By the reservoir being squeezed in the manner set out above, air can be extinguished from the reservoir by way of the bleeder valve.

Thus, to allow for such exit of air, prior to use, the cap can be removed from the bleeder valve. The reservoir is then squeezed to exit air from the reservoir through the bleeder valve. Once air has been extinguished from the reservoir (such as when liquid starts exiting from the bleeder valve), the cap is replaced. This then closes the bleeder valve.

It has been found that the provision of such a bleeder valve and cap prevents or at least reduces air pockets forming in the chamber 8, which can in some cases detract from the effectiveness and efficiency of the invention.

This invention has been described by way of example only, and it will be appreciated that improvements and variations may be made within the scope and spirit of the claims as appended hereto.

We claim:

1. An applicator including:
   a reservoir for matter to be applied;
   an applicator head comprising a chamber and elongate needle;
   the needle being at least partially surrounded by a generally elongate proboscis mounted for axial movement over the needle;
   at least one valving means being provided between the chamber and the needle;
   further valving means being provided between the reservoir and the chamber;
   triggering means being provided;
   actuation of said triggering means causing matter to be applied to be passed from the reservoir into the chamber;
   the proboscis being so mounted relative to the chamber and the needle, that on predetermined axial movement of the proboscis over the needle, at least an end of said needle is at least partially exposed and means between the chamber and needle is opened and means is provided to cause matter to pass from the chamber through said needle.

2. An applicator including:
   a housing adapted to releasably locate a reservoir and applicator head;
   the applicator head including a chamber and needle;
   the needle being at least partially surrounded by a generally elongate proboscis capable of axial movement relative to the needle; valving being provided between the chamber and the needle;
   further valving means being provided between the reservoir and the chamber;
   triggering means being provided;
   actuation of said triggering means causing matter to be applied to be passed from the reservoir into the chamber;
   the proboscis being so mounted relative to the chamber and needle, that on predetermined axial movement of the proboscis relative to the needle, valving means between the chamber and needle is opened and matter to be applied is caused to be passed from the chamber through the needle;

the housing including an upper body portion capable of releasably locating the applicator head;

a lower body support being spaced apart from the upper body portion so as to releasably locate the reservoir therebetween;

the body further including a rear upper body portion and a handle portion defining a grip opening;

triggering means being pivotally mounted to the handle portion, and means being provided to cause matter to be applied to pass from the chamber through said needle.

3. An applicator according to claim 2, wherein the proboscis includes valve actuating means; valving between said chamber and said needle including valve actuating means; axial movement of the proboscis relative to the needle, causing the proboscis valve actuating means to come into contact with the actuating means of the valve between the chamber and needle, such that the valve between the chamber and needle is caused to open.

4. An applicator according to claim 2, wherein the valve between the reservoir and the chamber is a non-return valve.

5. An applicator according to claim 2, wherein the chamber included at least one movable wall.

6. An applicator according to claim 2, wherein the chamber includes a movable wall in the form of a flexible diaphragm.

7. An applicator according to claim 2, wherein at least one wall of the chamber is in the form of a movable wall; actuating means being connected to the movable wall so as to move said wall inwardly and outwardly of the chamber; the actuating means being spring biased so as to urge the movable wall inwardly of the chamber.

8. An applicator according to claim 2, wherein the chamber is provided with a movable wall; actuating means being connected to the movable wall so as to move the wall inwardly and outwardly of the chamber; the actuating means being spring biased so as to urge the movable wall inwardly of the chamber; the triggering means being linked to the actuating means connected to the movable wall; operation of the triggering means causing the actuating means to move the movable wall outwardly of the chamber, so as to draw a shot or measure to be applied into the chamber.

9. An applicator according to claim 8, wherein the triggering means is connected by a lever arrangement to the actuating means of the movable wall of the chamber.

10. An applicator as claimed in claim 2 including a counting mechanism to indicate each shot or measure delivered, said counting mechanism being provided within the housing and including a display face viewable from exterior of the housing; an operating finger being provided; the triggering means being connected by a lever arrangement to the actuating means of the movable wall of the chamber; operation of the triggering means causing movement of the lever arrangement which actuates the operating finger of the counting mechanism.

11. An applicator according to claim 2, wherein at least one wall of the chamber is a movable wall, first actuating means attached to the movable wall and being releasably locatable within said upper body portion of the housing; the first actuating means being connectable to spring biased second actuating means within said housing; said second actuating means being connected by a lever arrangement to the triggering means; the arrangement being such that on location of the head member and the reservoir within the housing, and on connection of said first and second actuating means one to the other, operation of the triggering means will cause the lever arrangement to move the interconnected first and second actuating means against spring bias, drawing the movable wall outwardly of the chamber, thus opening the valving between the reservoir and the chamber and drawing a shot or measure of matter to be applied from the reservoir into the chamber, where it is held under pressure from said spring biased actuating means.

12. An applicator according to claim 2, wherein at least one wall of the chamber is a movable wall; actuating means being attached to the movable wall, a crank arm being connected to the end of the actuating means; triggering means being provided and mounting a pivot lever; the crank arm and pivot lever being engageable one with the other such that on the trigger being actuated, the engaged pivot lever and crank arm will cause the actuating means to move the movable wall outwardly of the chamber.

13. An applicator as claimed in any one of claims 1 or 2, wherein at least one wall of the chamber is a movable wall; actuating means being attached to the movable wall; a crank arm being connected to the end of the actuating means and extending into a flexible hook at a lower end thereof; triggering means being provided and mounting a pivot lever having upper and lower pivot arms; pivot stops being provided adjacent the upper and lower pivot arms to prevent free rotation of the pivot lever relative to the triggering means; the flexible hook of the crank arm being engageable with the upper pivot arm, such that actuation of the griggering means causes the engaged hook of the crank arm and the upper pivot arm to move the actuating means and movable wall outwardly of the chamber.

14. An applicator as claimed in any one of claims 1 or 2 wherein at least one wall of the chamber is a movable wall; actuating means being attached to the movable wall; a crank arm being connected to the end of the actuating means and extending into a flexible hook at a lower end thereof; triggering means being provided and mounting a pivot lever having upper and lower pivot arms; pivot stops being provided adjacent the upper and lower pivot arms to prevent free rotation of the pivot lever relative to the triggering means; the flexible hook of the crank arm being engaged with the upper pivot arm; the arrangement being such that actuation of the triggering means causes the engaged hook of the crank arm and the upper pivot arm to move the actuating means and movable wall outwardly of the chamber; abutment means being provided such that on the engaged flexible hook of the crank arm and upper pivot arm coming into contact therewith, the flexible hook of the crank arm is released from engagement with the upper pivot arm.

15. An applicator according to claim 2, wherein a bleeder valve is formed or provided in an upper wall of the chamber.

16. An applicator according to claim 2 wherein the proboscis includes valve actuating means; valving between said chamber and said needle including valve actuating means; axial movement of the proboscis relative to the needle, causing the proboscis valve actuating means to come into contact with the actuating means of the valve between the chamber and needle, such that the valve between the chamber and needle is caused to open.

17. An applicator according to claim 1 wherein the proboscis includes valve actuating means; valving between said chamber and said needle including valve actuating means; axial movement of the proboscis relative to the needle, causing the proboscis valve actuating means to come into contact with the actuating means of the valve between the chamber and needle, such that the valve between the chamber and needle is caused to open.

18. An applicator according to claim 1, wherein the valve between the reservoir and the chamber is a non-return valve.

19. An applicator according to claim 1, wherein the chamber includes at least one movable wall.

20. An applicator according to claim 1, wherein the chamber includes at least one movable wall.

21. An applicator according to claim 1, wherein the chamber includes a movable wall in the form of a flexible diaphragm.

22. An applicator according to claim 1, wherein the chamber includes a movable wall in the form of a flexible diaphragm.

23. An applicator according to claim 1, wherein at least one wall of the chamber is in the form of a movable wall; actuating means being connected to the movable wall so as to move said wall inwardly and outwardly of the chamber; the actuating means being spring biased so as to urge the movable wall inwardly of the chamber.

24. An applicator according to claim 1, wherein at least one wall of the chamber is in the form of a movable wall; actuating means being connected to the movable wall so as to move said wall inwardly and outwardly of the chamber; the actuating means being spring biased so as to urge the movable wall inwardly of the chamber.

25. An applicator according to claim 1, wherein the chamber is provided with a movable wall; actuating means being connected to the movable wall so as to move the wall inwardly and outwardly of the chamber; the actuating means being spring biased so as to urge the movable wall inwardly of the chamber; the triggering means being linked to the actuating means connected to the movable wall; operation of the triggering means causing the actuating means to move the movable wall outwardly of the chamber, so as to draw a shot or measure to be applied to the chamber.

26. An applicator according to claim 1, wherein the triggering means is connected by a lever arrangement to the actuating means of the movable wall of the chamber.

27. An applicator according to claim 1, wherein at least one wall of the chamber is a movable wall; first actuating means attached to the movable wall and being releasably locatable within said upper body portion of the housing; the first actuating means being connectable to spring biased second actuating means within said housing; second actuating means being connected by a lever arrangement to the triggering means; the arrangement being such that on location of the head member and the reservoir within the housing, and on connection of said first and second actuating means one to the other, operation of the triggering means will cause the level arrangement to move the interconnected first and second actuating means against spring bias, drawing the movable wall outwardly of the chamber, thus opening the valving between the reservoir and the chamber and drawing a shot or measure of matter to be applied from the reservoir into the chamber, where it is held under pressure from said spring biased actuating means.

28. An applicator according to claim 1, wherein at least one wall of the chamber is a movable wall; first actuating means attached to the movable wall and being releasably locatable within said upper body portion of the housing; the first actuating means being connectable to spring biased second actuating means within said housing; second actuating means being connected by a lever arrangement to the triggering means; the arrangement being such that on location of the head member and the reservoir within the housing, and on connection of said first and second actuating means one to the other, operation of the triggering means will cause the lever arrangement to move the interconnected first and second actuating means against spring bias, drawing the movable wall outwardly of the chamber, thus opening the valving between the reservoir and the chamber and drawing a shot or measure of matter to be applied from the reservoir into the chamber, where it is held under pressure from said spring biased actuating means.

29. An applicator according to claim 1, wherein at least one wall of the chamber is a movable wall; actuating means being attached to the movable wall, a crank arm being connected to the end of the actuating means; triggering means being provided and mounting a pivot lever; the crank arm and pivot lever being engageable one with the other such that on the trigger being actuated, the engaged pivot lever and crank arm will cause the actuating means to move the movable wall outwardly of the chamber.

30. An applicator according to claim 1, wherein a bleeder valve is formed or provided in an upper wall of the chamber.

31. An applicator according to claim 1, wherein a bleeder valve is formed or provided in an upper wall of the chamber.

32. An applicator comprising a head containing a chamber and an elongate hollow needle, said needle being fixed to the head and having one end adjacent the chamber, a generally elongate proboscis being mounted about and at least partially surrounding the needle and being adapted for axial movement over the needle, valve means being provided between said one end of the needle and the chamber, and being operable to provide communication between the chamber and the needle, said proboscis being so mounted relative to the chamber and needle that on predetermined axial movement of the proboscis rearwardly over the needle, by application of pressure to its forward end, the other end of the needle is at least partially exposed and said valve means opened and means being provided to cause a dosage to be applied to pass from the chamber through the needle when the valve means is opened.

33. An applicator as claimed in claim 32 wherein the applicator is a multiple dosage applicator, said chamber being adapted to receive a dosage to be applied.

34. An applicator as claimed in claim 32 comprising means operable when pressure at the forward end of the proboscis is released to cause the proboscis to move forwardly over the needle to at least partially surround it and to close the valve means.

35. An applicator as claimed in claim 33, comprising a reservoir for receiving a plurality of dosages and a one-way valve connecting the reservoir to the chamber for supplying one dosage at a time to said chamber.

36. A multiple dosage applicator comprising a head containing a chamber for receiving a dosage to be applied, and an elongate hollow needle being fixed to the head with one end adjacent the chamber, a generally elongate proboscis mounted about and at least partially surrounding the needle and being adapted for axial movement over the needle, valve means being provided between said one end of the needle and the chamber, and being operable to provide communication between the chamber and the needle so that on predetermined axial movement of the proboscis rearwardly over the needle, by application of pressure to its forward end, the other end of the needle is at least partially exposed and said valve means opened and means being provided to cause the dosage to be applied to pass from the chamber through the needle when the valve means is opened.

37. An applicator comprising an applicator head which includes a chamber and an elongate hollow needle, said needle having one end located adjacent the chamber, a generally elongate proboscis being mounted about the needle and being capable of axial rearward movement over the needle and relative to the chamber, valve means being provided between the needle and the chamber and being operable to provide communication between the needle and chamber, said proboscis being so mounted relative to the needle and chamber that predetermined axial movement of the proboscis rearwardly over the needle and relative to the chamber, by application of pressure to the forward end of the proboscis, at least partially exposes the other end of the said needle, said valve means between the chamber and needle being thereafter operable so as to permit passage of matter to be applied from the chamber through the needle, means being provided to cause said matter to pass from the chamber through the needle.

38. An applicator as claimed in claim 37, wherein the applicator is a multiple dosage applicator, said chamber being adapted to receive a dosage to be applied.

39. An applicator as claimed in claim 37, comprising means operable when pressure at the forward end of the proboscis is released, to cause the proboscis to move forwardly over and relative to the needle, to at least partially surround said needle and to close the valve means.

40. An applicator as claimed in claim 37, comprising a reservoir for receiving a plurality of dosages and a one-way valve connecting the reservoir to the chamber for supplying one dosage at a time to said chamber.

41. An applicator as claimed in claim 37, wherein the chamber includes at least one movable wall.

42. An applicator as claimed in claim 37, wherein the chamber includes a movable wall in the form of a flexible diaphragm.

43. An applicator as claimed in claim 37, wherein a bleeder valve is formed or provided in an upper wall of the chamber.

* * * * *